(12) United States Patent
Danitz et al.

(10) Patent No.: US 7,785,252 B2
(45) Date of Patent: Aug. 31, 2010

(54) ARTICULATING SHEATH FOR FLEXIBLE INSTRUMENTS

(75) Inventors: David J. Danitz, San Jose, CA (US); Cameron D. Hinman, Thurmond, NC (US)

(73) Assignee: Novare Surgical Systems, Inc., Cupertino, CA (US)

( * ) Notice: Subject to any disclaimer, the term of this patent is extended or adjusted under 35 U.S.C. 154(b) by 1266 days.

(21) Appl. No.: 10/997,245

(22) Filed: Nov. 23, 2004

(65) Prior Publication Data

US 2006/0111615 A1    May 25, 2006

(51) Int. Cl.
*A61B 1/00* (2006.01)
(52) U.S. Cl. .................. 600/142; 600/139; 600/140; 600/141; 600/146; 600/150; 604/95.01; 604/95.04; 138/118; 138/155
(58) Field of Classification Search ............... 600/139, 600/141–142
See application file for complete search history.

(56) References Cited

U.S. PATENT DOCUMENTS

| | | | |
|---|---|---|---|
| 1,820,463 A | 8/1931 | Klein | |
| 3,060,972 A | 10/1962 | Sheldon | |
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A * | 12/1988 | Allred et al. ............... | 600/141 |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,174,276 A | 12/1992 | Crockard | |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |

(Continued)

FOREIGN PATENT DOCUMENTS

EP    0 165 718    12/1985

(Continued)

OTHER PUBLICATIONS

International Search Report mailed on Dec. 19, 2005 for PCT Application No. PCT/US2005/033260.

(Continued)

*Primary Examiner*—Matthew J Kasztejna
(74) *Attorney, Agent, or Firm*—Shay Glenn LLP (57) ABSTRACT

A sheath useful for remote steering, guidance and/or manipulation of a flexible instrument, including e.g. an endoscope, received through the sheath.

16 Claims, 9 Drawing Sheets

U.S. PATENT DOCUMENTS

| | | | |
|---|---|---|---|
| 5,381,782 | A | 1/1995 | DeLaRama et al. |
| 5,403,342 | A | 4/1995 | Tovey et al. |
| 5,405,344 | A | 4/1995 | Williamson et al. |
| 5,425,743 | A | 6/1995 | Nicholas |
| 5,441,494 | A | 8/1995 | Ortiz |
| 5,454,827 | A | 10/1995 | Aust et al. |
| 5,476,479 | A | 12/1995 | Green et al. |
| 5,486,154 | A | 1/1996 | Kelleher |
| 5,490,819 | A | 2/1996 | Nicholas et al. |
| 5,498,256 | A | 3/1996 | Furnish |
| 5,520,678 | A | 5/1996 | Heckele et al. |
| 5,522,788 | A | 6/1996 | Kuzmak |
| 5,549,636 | A | 8/1996 | Li |
| 5,562,699 | A | 10/1996 | Heimberger et al. |
| 5,570,919 | A | 11/1996 | Eusebe |
| 5,599,151 | A * | 2/1997 | Daum et al. ............ 414/7 |
| 5,609,601 | A | 3/1997 | Kolesa et al. |
| 5,620,415 | A | 4/1997 | Lucey et al. |
| 5,624,398 | A | 4/1997 | Smith et al. |
| 5,626,608 | A | 5/1997 | Cuny et al. |
| 5,632,432 | A | 5/1997 | Schulze et al. |
| 5,643,294 | A | 7/1997 | Tovey et al. |
| 5,647,743 | A | 7/1997 | Schmitt |
| 5,702,408 | A | 12/1997 | Wales et al. |
| 5,704,534 | A | 1/1998 | Huitema et al. |
| 5,713,505 | A | 2/1998 | Huitema |
| 5,716,352 | A | 2/1998 | Viola et al. |
| 5,759,151 | A | 6/1998 | Sturges |
| 5,792,164 | A | 8/1998 | Lakatos et al. |
| 5,807,376 | A | 9/1998 | Viola et al. |
| 5,813,813 | A | 9/1998 | Daum et al. |
| 5,823,066 | A | 10/1998 | Huitema et al. |
| 5,827,323 | A | 10/1998 | Klieman et al. |
| 5,836,960 | A | 11/1998 | Kolesa et al. |
| 5,846,183 | A | 12/1998 | Chilcoat |
| 5,873,817 | A | 2/1999 | Kokish et al. |
| 5,899,425 | A | 5/1999 | Corey, Jr. et al. |
| 5,916,146 | A | 6/1999 | Allotta et al. |
| 5,916,147 | A | 6/1999 | Boury |
| 5,921,956 | A | 7/1999 | Grinberg et al. |
| 5,938,678 | A | 8/1999 | Zirps et al. |
| 5,961,532 | A | 10/1999 | Finley et al. |
| 6,019,722 | A | 2/2000 | Spence et al. |
| 6,050,996 | A | 4/2000 | Schmaltz et al. |
| 6,161,543 | A | 12/2000 | Cox et al. |
| 6,250,532 | B1 | 6/2001 | Green et al. |
| 6,270,453 | B1 | 8/2001 | Sakai |
| 6,464,704 | B2 | 10/2002 | Schmaltz et al. |
| 6,471,641 | B2 | 10/2002 | Sakamoto |
| 6,471,696 | B1 | 10/2002 | Berube et al. |
| 6,482,149 | B1 | 11/2002 | Torii |
| 6,491,626 | B1 | 12/2002 | Stone et al. |
| 6,571,042 | B1 | 5/2003 | Kordahi |
| 6,626,824 | B2 | 9/2003 | Ruegg et al. |
| 6,635,071 | B2 | 10/2003 | Boche et al. |
| 6,638,213 | B2 | 10/2003 | Ogura et al. |
| 6,638,287 | B2 | 10/2003 | Danitz et al. |
| RE38,335 | E | 11/2003 | Aust et al. |
| 6,641,528 | B2 | 11/2003 | Torii |
| 6,644,532 | B2 | 11/2003 | Green et al. |
| 6,666,854 | B1 | 12/2003 | Lange |
| 6,669,254 | B2 | 12/2003 | Thom et al. |
| 6,676,676 | B2 | 1/2004 | Danitz et al. |
| 6,682,541 | B1 | 1/2004 | Gifford et al. |
| 6,743,239 | B1 | 6/2004 | Kuehn et al. |
| 6,746,443 | B1 | 6/2004 | Morley et al. |
| 6,749,560 | B1 | 6/2004 | Konstorum et al. |
| 6,752,823 | B2 | 6/2004 | Prestel |
| 6,764,445 | B2 | 7/2004 | Ramans et al. |
| 6,773,327 | B1 | 8/2004 | Felice et al. |
| 6,817,972 | B2 | 11/2004 | Snow |
| 6,817,974 | B2 * | 11/2004 | Cooper et al. ............ 600/142 |
| 6,824,548 | B2 | 11/2004 | Smith et al. |
| 6,843,947 | B2 | 1/2005 | Sixto, Jr. et al. |
| 6,858,005 | B2 * | 2/2005 | Ohline et al. ............ 600/141 |
| 6,902,560 | B1 | 6/2005 | Morley et al. |
| 6,942,613 | B2 | 9/2005 | Ewers et al. |
| 6,945,979 | B2 | 9/2005 | Kortenbach et al. |
| 6,960,162 | B2 | 11/2005 | Saadat et al. |
| 6,960,163 | B2 | 11/2005 | Ewers et al. |
| 6,976,969 | B2 | 12/2005 | Messerly |
| 6,994,700 | B2 | 2/2006 | Elkins et al. |
| 7,138,976 | B1 | 11/2006 | Bouzit et al. |
| 7,147,650 | B2 * | 12/2006 | Lee ............ 606/205 |
| 7,553,275 | B2 | 6/2009 | Padget et al. |
| 2001/0023313 | A1 | 9/2001 | Ide |
| 2001/0042766 | A1 | 11/2001 | Ming-Shun |
| 2002/0096177 | A1 | 7/2002 | Toti et al. |
| 2002/0111604 | A1 | 8/2002 | Doyle et al. |
| 2002/0156497 | A1 | 10/2002 | Nagase et al. |
| 2002/0161281 | A1 | 10/2002 | Jaffe et al. |
| 2002/0177750 | A1 | 11/2002 | Pilvisto |
| 2003/0036748 | A1 | 2/2003 | Cooper et al. |
| 2003/0050649 | A1 | 3/2003 | Brock et al. |
| 2003/0078644 | A1 | 4/2003 | Phan |
| 2003/0109898 | A1 | 6/2003 | Schwarz et al. |
| 2003/0114838 | A1 | 6/2003 | O'Neill et al. |
| 2003/0135204 | A1 | 7/2003 | Lee et al. |
| 2003/0149338 | A1 | 8/2003 | Francois et al. |
| 2003/0153902 | A1 | 8/2003 | Doyle et al. |
| 2003/0229271 | A1 | 12/2003 | Briscoe et al. |
| 2003/0233026 | A1 | 12/2003 | Saadat et al. |
| 2004/0054322 | A1 | 3/2004 | Vargas |
| 2004/0138529 | A1 | 7/2004 | Wiltshire et al. |
| 2004/0138700 | A1 | 7/2004 | Cooper et al. |
| 2004/0236316 | A1 | 11/2004 | Danitz et al. |
| 2005/0090809 | A1 | 4/2005 | Cooper et al. |
| 2005/0096694 | A1 | 5/2005 | Lee |
| 2005/0107667 | A1 | 5/2005 | Danitz et al. |
| 2005/0119527 | A1 * | 6/2005 | Banik et al. ............ 600/117 |
| 2005/0251112 | A1 | 11/2005 | Danitz et al. |
| 2005/0273084 | A1 | 12/2005 | Hinman et al. |
| 2005/0273085 | A1 | 12/2005 | Hinman et al. |
| 2006/0009759 | A1 | 1/2006 | Christian et al. |
| 2006/0020287 | A1 | 1/2006 | Lee et al. |
| 2006/0036255 | A1 | 2/2006 | Pond et al. |
| 2006/0058582 | A1 | 3/2006 | Maahs et al. |
| 2006/0094931 | A1 | 5/2006 | Danitz et al. |
| 2006/0111209 | A1 | 5/2006 | Hinman et al. |
| 2006/0111210 | A1 | 5/2006 | Hinman |
| 2006/0111616 | A1 | 5/2006 | Danitz |
| 2006/0199999 | A1 | 9/2006 | Ikeda et al. |
| 2007/0250113 | A1 | 10/2007 | Hegeman et al. |
| 2007/0287993 | A1 | 12/2007 | Hinman |

FOREIGN PATENT DOCUMENTS

| | | |
|---|---|---|
| EP | 0 598 618 A2 | 5/1994 |
| EP | 0 836 833 A2 | 4/1998 |
| EP | 0 836 833 A3 | 4/1998 |
| EP | 1 132 041 A2 | 9/2001 |
| EP | 1 395 398 B1 | 3/2004 |
| JP | H06-262549 | 9/1994 |
| JP | 01-299768 | 10/2001 |
| WO | WO 01/10292 A1 | 2/2001 |
| WO | WO-02/13682 A1 | 2/2002 |
| WO | WO-2004/019769 A1 | 3/2004 |
| WO | WO-2004/105578 A2 | 12/2004 |
| WO | WO-2004/105578 A3 | 12/2004 |
| WO | WO-2004/105578 C2 | 12/2004 |
| WO | WO 2005/067785 A1 | 7/2005 |
| WO | WO-2005/120326 A2 | 12/2005 |
| WO | WO-2005/120326 A3 | 12/2005 |
| WO | WO 2005/120327 A2 | 12/2005 |

| | | | |
|---|---|---|---|
| WO | WO-2005/120327 A3 | 12/2005 | |
| WO | WO-2006/057699 A1 | 6/2006 | |
| WO | WO-2006/057700 A1 | 6/2006 | |
| WO | WO-2006/057702 A2 | 6/2006 | |
| WO | WO 2006/073581 A1 | 7/2006 | |

OTHER PUBLICATIONS

U.S. Appl. No. 11/344,465, filed Jan. 30, 2006 for Danitz, 28 pages.

Hegeman et al; U.S. Appl. No. 11/787,201 entitled "Articulating tool with improved tension member system" filed Apr. 16, 2007.

Hinman et al; U.S. Appl. No. 11/787,599 entitled "Tool with end effector force limiter," filed Apr. 16, 2007.

Hinman, Cameron; U.S. Appl. No. 11/787,605 entitled "Tool with multi-state ratcheted end effector," filed Apr. 16, 2007.

Danitz et al.; U.S. Appl. No. 12/109,333 entitled "Articulating instrument," filed Apr. 24, 2008.

Isbell Jr., Lewis; U.S. Appl. No. 12/542,589 entitled "Instrument with articulation lock," filed Aug. 17, 2009.

Hinman, Cameron; U.S. Appl. No. 12/508,478 entitled "Articulating mechanism," filed Jul. 23, 2009.

Hinman et al.; U.S. Appl. No. 12/725,377 entitled "Articulating mechanism with flex-hinged links," filed Mar. 16, 2010.

\* cited by examiner

ARTICULATING SHEATH FOR FLEXIBLE INSTRUMENTS

BACKGROUND OF THE INVENTION

This invention relates to sheaths for the remote steering, guidance, navigation and manipulation of flexible instruments, such as endoscopes.

Endoscopic procedures typically employ endoscopic instruments that are maneuvered within or towards a target organ or tissue from a position outside the body. Examples of endoscopic procedures include sigmoidoscopy, colonoscopy, esophagogastroduodenoscopy, and bronchoscopy. Typically flexible endoscopes, which have flexible insertion tubes, are used for such procedures. The insertion tube of the endoscope is advanced by pushing it forward, and retracted by pulling it back. The tip of the tube may be directed by twisting and general up/down and left/right movements. Oftentimes, this limited range of motion makes it difficult to negotiate acute angles, creating patient discomfort and increasing the risk of trauma to surrounding tissues.

Endoscopes can also be employed in laparoscopic procedures. Such procedures typically involve introducing a trocar into a person's body and then inserting an endoscope tube through the trocar to the desired location. Rigid endoscopes, i.e., endoscopes having a less flexible, more rigid insertion tube (also sometimes referred to as laparascopes) are more typically used in laparoscopic procedures, as the need to advance such endoscopes through constricted anatomical structures is less pronounced. Maneuverability of the endoscope deployed in this fashion is limited, with little ability to navigate the endoscope independent of moving the insertion trocar.

There have been many attempts to design endoscopes as well as catheters, with improved steerability, however, the range of motion is generally limited. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato). U.S. Pat. No. 5,916,147 to Boury et al. discloses a steerable catheter having four wires that run within the catheter wall. Each wire terminates at a different part of the catheter. The proximal end of the wires extend loosely from the catheter so that the physician may pull them. The physician is able to shape and thereby steer the catheter by selectively placing the wires under tension.

Steerable endoscopes have improved range of motion as compared to non-steerable flexible endoscopes or rigid endoscopes, but their range of motion is still generally limited. Further, these devices can be laborious to use, pulling each wires separately as in Boury et al., and may require a significant amount of training to become proficient in maneuvering the device through the patient's anatomy, as in the case of knob and pulley mechanisms. In addition, steerable endoscopes are expensive to maintain. Consequently, it would be advantageous to provide an easier to use, more cost-effective system to improve steering, navigation, guidance and manipulation of conventional flexible endoscopes.

BRIEF SUMMARY OF THE INVENTION

The present invention provides for a sheath that can receive a flexible instrument, e.g., flexible endoscopes, suction tubes, irrigation tubes, and tools with flexible shafts, such as, endoscopic tools (i.e., tools adapted for delivery through the working channel of an endoscope), lasers and energy sources, and that can route the instrument through the sheath such that a portion of the instrument can extend to or past the distal end of the sheath. The sheath can be manually manipulated from its proximal end to remotely steer, guide, manipulate and/or navigate the insertion tube at the distal end of the sheath.

In one variation of the invention, a sheath is provided having an elongate shaft and proximal and distal sections having multiple pairs of links, with one member of a pair located on the proximal section and the other of the pair located on the distal section. The sheath further includes a lumen that extends at least partially through the shaft and which opens through the distal section of the shaft. An inlet port in communication with the lumen is located between the proximal and distal sections of the sheath. The inlet port and shaft lumen allows for the insertion tube of an endoscope to extend through the sheath to the distal end of the sheath. The sheath further includes one or more sets of cables connecting the links of at least one discrete pair to one another, such that movement of one link of the connected pair causes corresponding relative movement of the other link of the pair. In further variations, multiple sets of cables are included, with each set connecting the links of a discrete pair. Movement of the proximal section results in corresponding movement of the distal section.

A wide variety of link systems can be used to form the proximal and distal sections of the sheath. In one variation of the invention, a link system is provided where the links form flexible segments. The flexible segments comprise a unit of at least one link and at least one flexible hinge, with adjacent flexible segments joined by flexible hinges. Pairs of flexible segments form the proximal and distal sections. Cables connecting the flexible segments of at least one discrete pair to one another, such that movement of one flexible segment of the connected pair causes corresponding relative movement of the other flexible segment of the pair The invention further provides methods of introducing, e.g., a flexible endoscope into a patient's body by inserting the sheath at a desired location and advancing the endoscope through the inlet port and into the sheath. In certain variations, introduction of the sheath can be aided through the use of a trocar.

DETAILED DESCRIPTION

As previously described, sheaths according to the invention are configured to receive and pass a flexible instrument through the sheath such that the tip of the instrument can emerge from the distal end of the sheath. The proximal and distal sections of the sheath are adapted such that movement or articulation of the proximal section produces corresponding movement or articulation of the distal section. For purposes of illustration only, such a sheath will now be described with respect to its use with a flexible endoscope, but it will be understood that use with a variety of flexible instruments is contemplated. Typically for use with a flexible endoscope, the sheath can be inserted to a desired location of a patient's body and the flexible endoscope is introduced into the sheath. Alternatively the endoscope can first be introduced into the sheath and the combination advanced together. Movement of the distal section of the sheath, which is controlled by the proximal section, moves the tip end of the endoscope insertion tube, thus moving the tip of the endoscope. Thus the endoscope can be easily steered, maneuvered, and guided by simple manipulation of the proximal section of the sheath, greatly simplifying navigation of a standard flexible endoscope, and allowing for easy and enhanced maneuverability of the endoscope when deployed, e.g., in a patient's body, whether in conventional endoscopic or laproscopic use.

The sheath will typically include an elongate shaft separating the proximal and distal sections. The shaft can be relatively stiff or rigid for laparoscopic use or it may be more flexible for endoscopic use. The proximal and distal sections will typically have multiple pairs of links, with one member of a pair located on the proximal section and the other of the pair located on the distal section. The terms "link" as used herein refer to a discrete portion or defined area at one end of the sheath that corresponds to another discrete portion or defined area at the opposite end of the sheath. The links are generally, but need not be cylindrical, and are generally axially aligned relative to one another, in an unarticulated condition. In any event, the sheath will include a plurality of links or segments that are members of discrete pairs, with one link of each pair being situated at the proximal section, and the other link or segment at the distal section. Sets of connecting cables connect the links of a discrete pair to one another so that movement of one link of a pair causes a corresponding movement of the other link or segment in the pair. A variety of link systems and connecting cables are compatible for forming the proximal and distal sections of the sheath, including but not limited to those described in pending and commonly owned U.S. application Ser. No. 10/444,769, filed on May 23, 2003, U.S. application Ser. No. 10/928,479, filed on Aug. 26, 2004, and U.S. application Ser. No. 10/948,911, filed on Sep. 24, 2004, and U.S. application Ser. No. 10/997,372 entitled "Articulating Mechanisms and Link Systems With Torque Transmission In Remote Manipulation of Instruments and Tools", filed Nov. 23, 2004, incorporated herein by reference in their entirety. As used herein, the term "active link" or "active link pair" refers to links that are directly connected to one another by a cable set. The term "spacer link" or "spacer link pair" refers to links that are not directly connected by a cable set. Spacer links can nevertheless be disposed between active links and provide for the passage of cable sets that connect active links. The ability to independently manipulate individual links allows for the proximal and distal sections to readily form complex three-dimensional configurations and geometries, in order to easily guide and navigate the endoscope insertion tube.

In certain variations of the invention, the proximal and distal sections of the sheath will include multiple pairs of flexible segments, such as those described in commonly owned and pending U.S. application Ser. No. 10/948,911, filed on Sep. 24, 2004. Such flexible segments usually include one or more adjacent links connected by flexible hinges that bend or flex. A flexible segment capable of movement in two dimensions with a single degree of freedom can have a single flexible hinge that connects two links. Alternatively, two or more flexible hinges can connect two links where the hinges are aligned in parallel. A flexible segment capable of movement in three dimensions with two degrees of freedom can have two flexible hinges oriented at an acute angle to one another connecting to three links. For a maximum three-dimensional range of motion, the angle will be orthogonal. A flexible segment pair refers to a flexible segment at one end section of the sheath that corresponds to a flexible segment at the other end section of the sheath. In order to achieve the greatest freedom of motion in three dimensions, at least one flexible hinge of the sheath is oriented orthogonal to at least one other hinge of the mechanism. However, the invention also contemplates configurations where flexible hinges are oriented parallel or are offset at any acute angle. As used herein, the term "active flexible segment" or "active flexible segment pair" refers to flexible segments that are directly connected to one another by a cable set. The term "spacer flexible segment" or "spacer flexible segment pair" refers to flexible segments that are not directly connected by a cable set. Spacer flexible segments can nevertheless be disposed between active flexible segments and provide for the passage of cable sets that connect active flexible segments.

Figure 1:
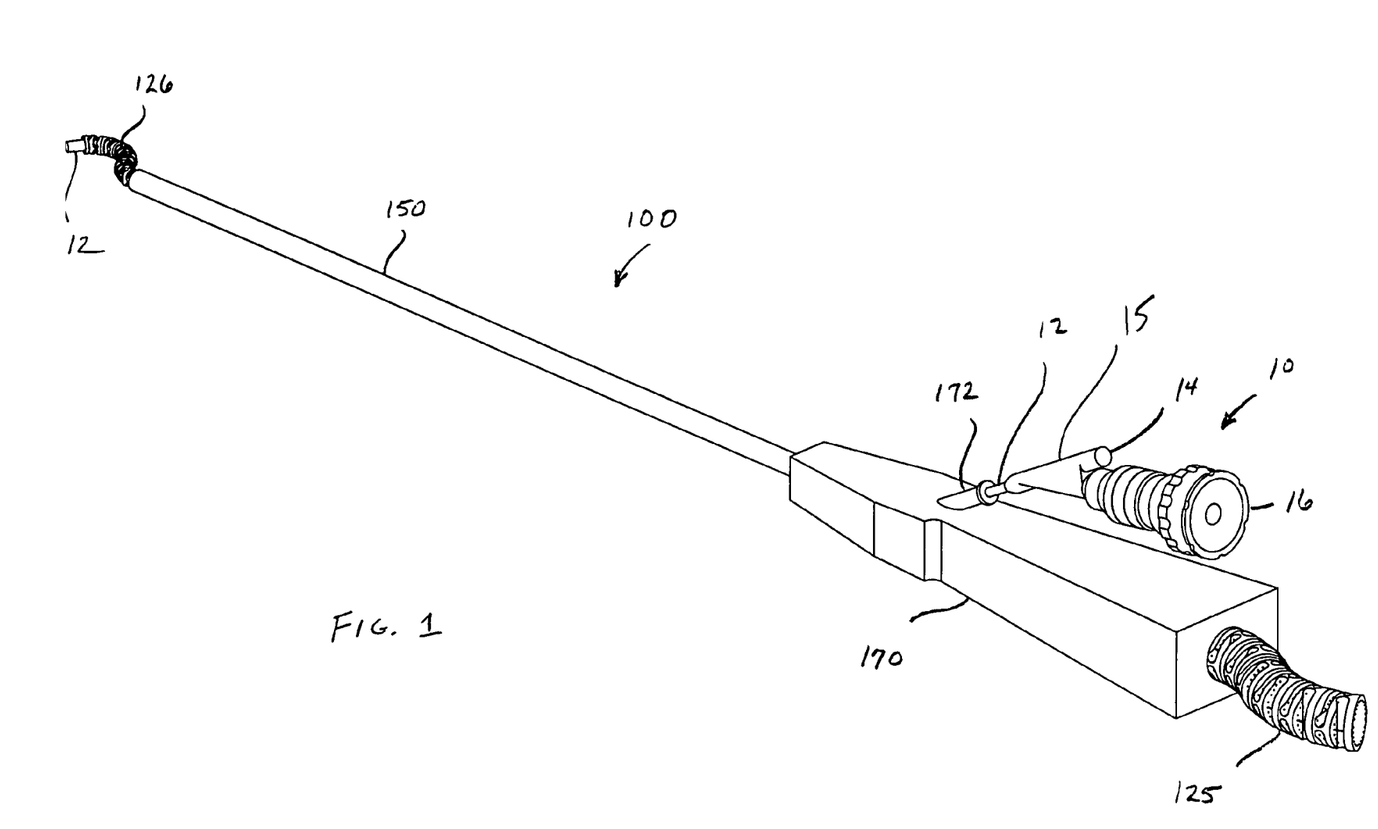
FIG. 1 is a perspective view of a sheath according to one embodiment of the invention, in an articulated position, with a flexible endoscope passing through the sheath.
Figure 2:
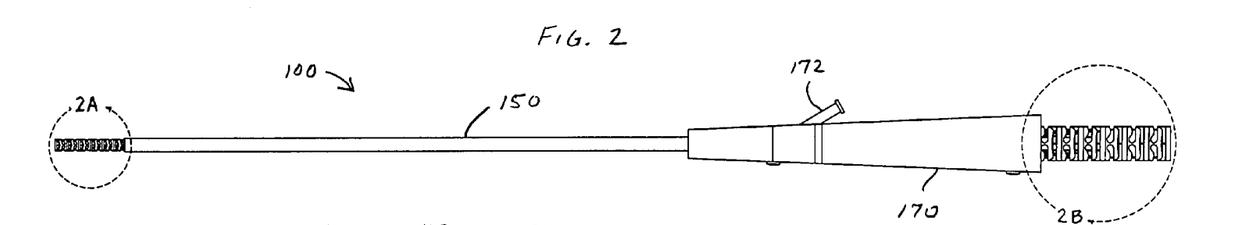
FIG. 2 is a side view of the sheath of FIG. 1.

FIG. 1 depicts an embodiment of a sheath according to the present invention with an endoscope deployed through the sheath. Sheath 100 includes elongate shaft 150, handle 170, proximal section 125 and distal section 126. Endoscope 10 includes camera/video coupler 16, port 14 for accessing the working channel of the endoscope, and insertion tube 12 extending from body 15 of the endoscope. Inlet port 172 extends from handle 170 and receives insertion tube 12 of endoscope 10. The insertion tube passes through the inlet port 172 and through shaft 150, with the tip of insertion tube 12 exiting from distal section 126 of the sheath. As depicted in FIG. 1, sheath 100 is shown in an articulated position, with the distal section in an articulated position that corresponds to that of the proximal section. FIG. 2 shows the sheath in the straight, unarticulated configuration.

Figure 2A:
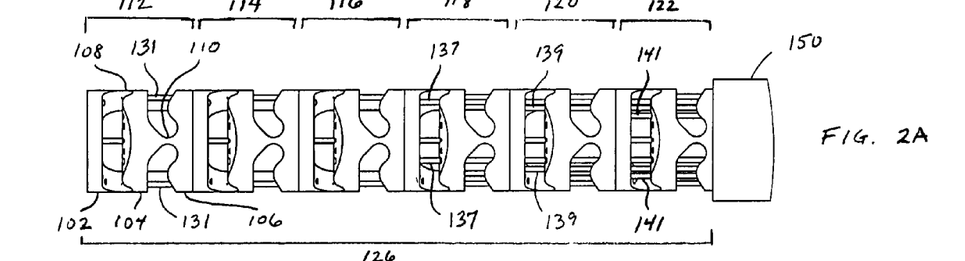
FIGS. 2A and 2B are enlarged views of the distal end and proximal end sections of the sheath of FIG. 2 designated 2A and 2B, respectively.
Figure 2B:
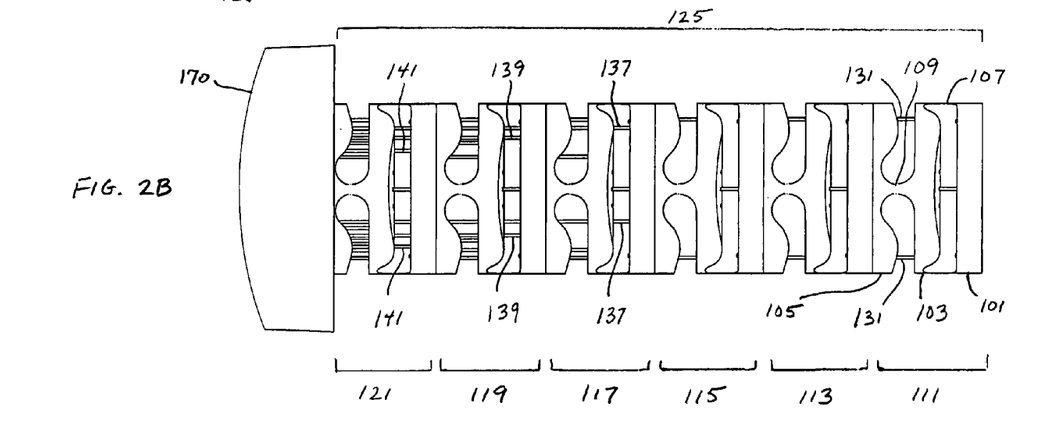
Figure 3A:
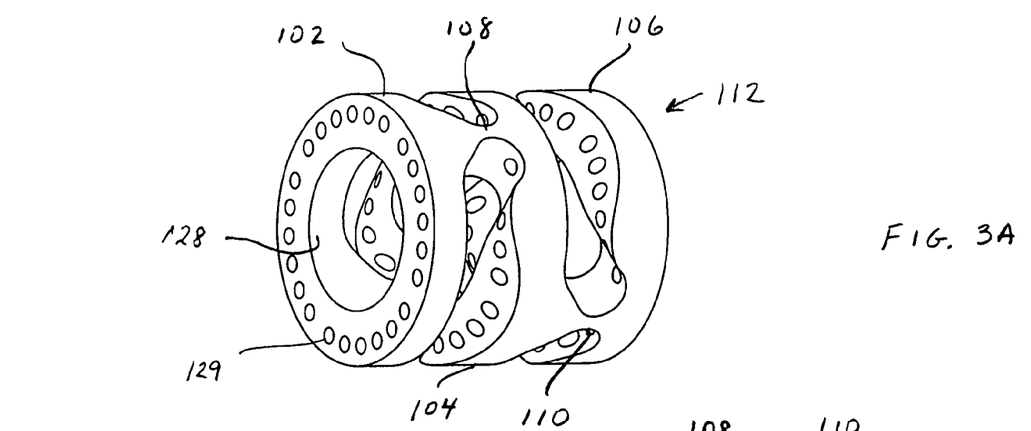
FIGS. 3A-3C show perspective, side, and end views, respectively, of a flexible segment that forms a portion of the distal section of FIG. 2A.
Figure 3B:
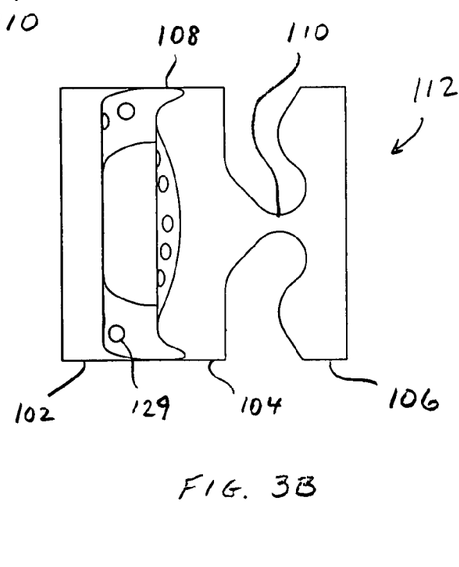
Figure 3C:
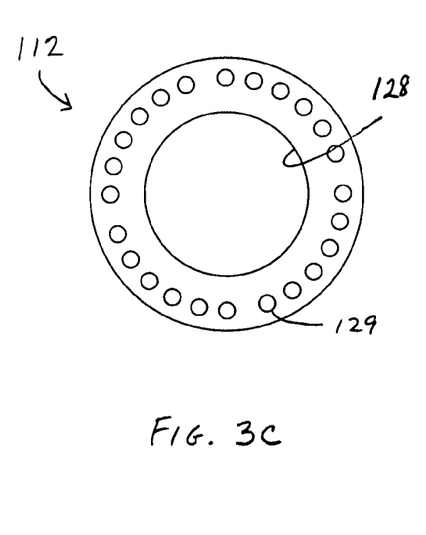

FIGS. 2A and 2B depict proximal and distal sections 125 and 126 in greater detail. Proximal and distal sections 125 and 126 are formed of a plurality of flexible segments. Flexible segments 111 and 112, 113 and 114, 115 and 116, 117 and 118, 119 and 120, and 121 and 122, respectively, are each members of a discrete pair, with one flexible segment of a pair (111, 113, 115, 117, 119 or 121) at proximal section 125 with the other (112, 114, 116, 118, 120 or 122) at distal section 126. As depicted, flexible segment 111 at proximal section 121 is formed of links 101, 103 and 105 connected by flexible hinges 107 and 109 oriented orthogonal to each other. Cable channels are located and pass through the periphery of each link for accepting passage and connection of cable sets. The distal section flexible segments also include a central channel 128 running through the longitudinal axis of the flexible segments of the distal section to accommodate passage of the endoscope, as further detailed herein. Flexible segment 112 is depicted in greater detail in FIGS. 3A-3C, and more clearly depict central channel 128 and cable channels 129 of the flexible segments. Paired flexible segment 112 at distal section 126 similarly is formed of links 102, 104 and 106 connected by flexible hinges 108 and 110 oriented orthogonal to one another and likewise include similar cable channels and can also include a central channel. The remaining flexible segments of both the proximal section (113, 115, 117, 119, and 121) and distal section (114, 116, 118, 120, and 122) have the same configuration with the last link of one segment also functioning as the first link of the next segment. And as shown, each flexible hinge is oriented orthogonal to adjacent hinges. As previously noted flexible segments of such configuration move in two degrees of freedom and are moveable in three dimensions. The proximal flexible segments (111, 117, 119 and 121) are connected to the distal flexible segments (112, 118, 120 and 122) by sets of cables 131, 137, 139 and 141, respectively. These flexible segment pairs are thus active flexible segments. Flexible segments 113 and 114, and 115 and 116 are not directly connected by a cable set and thus function as spacer segments. The depicted configuration of active and spacer segments is for illustration only, and it is to be understood that arrangements and combinations can vary, depending on the application.

Each active flexible segment at the proximal section of the sheath is connected to its corresponding active flexible segment at the distal section by at least one and preferably two or more cables. Each cable set may be made up of at least one and preferably two or more cables. As noted, movement of one active flexible segment pair is controlled by its corresponding cable set and is independent of any other flexible segment pair. In certain variations, for example, a cable set will include three cables spaced 120 degrees apart. By using a set of three cables to connect an active flexible segment having at least one flexible hinge oriented orthogonal to at least one other flexible hinge, each active flexible segment pair can be manipulated or moved in three degrees of freedom, independently of any other active pairs. These three degrees of freedom include up/down motion, left/right motion, and rotational or "rolling" motion (whether or not the flexible segment is in a straight or bent configuration). By combining a plurality of active flexible segments, multiple degrees of freedom are achieved, allowing the proximal and distal sections of the sheath to be shaped into various complex configurations.

The use of flexible segments in proximal and distal sections 125 and 126 has certain advantages. One is simply the flexibility provided by the flexible segments. For even greater flexibility, flexible segments combining two flexible hinges between links, such as those described in pending and commonly owned U.S. application Ser. No. 10/948,911, filed on Sep. 24, 2004, incorporated herein by reference in its entirety, may be used. Another advantage is ease of manufacture and assembly, as the proximal and distal sections can be manufactured as continuous pieces having multiple links connected by the flexible hinges. A further advantage is an increased ability to transmit torque along the sheath. However, there are other link systems that can be used in the sheaths of the present invention that also transmit torque, including but not limited to the link systems described in pending and commonly owned U.S. applicaton Ser. No. 10/997,372, entitled "Articulating Mechanisms and Link Systems With Torque Transmission In Remote Manipulation of Instruments and Tools", filed Nov. 23, 2004, incorporated herein in its entirety.

Variations of the sheath can also include proximal section links or segments that may include a channel for receiving a locking rod that can secure and retain the proximal end of the sheath in a fixed position. Instead of a rod, a locking sleeve may be fitted over the proximal end of the sheath to secure and retain the proximal end in a fixed position. This may be advantageous in situations where it is desirous to maintain the endoscope in a fixed location, once it has been steered to that location through use of the sheath. Other mechanisms for locking the sheath in a fixed, articulated position include but are not limited to those described in U.S. application Ser. No. 10/928,479, filed on Aug. 26, 2004, incorporated herein in its entirety.

Figure 4:
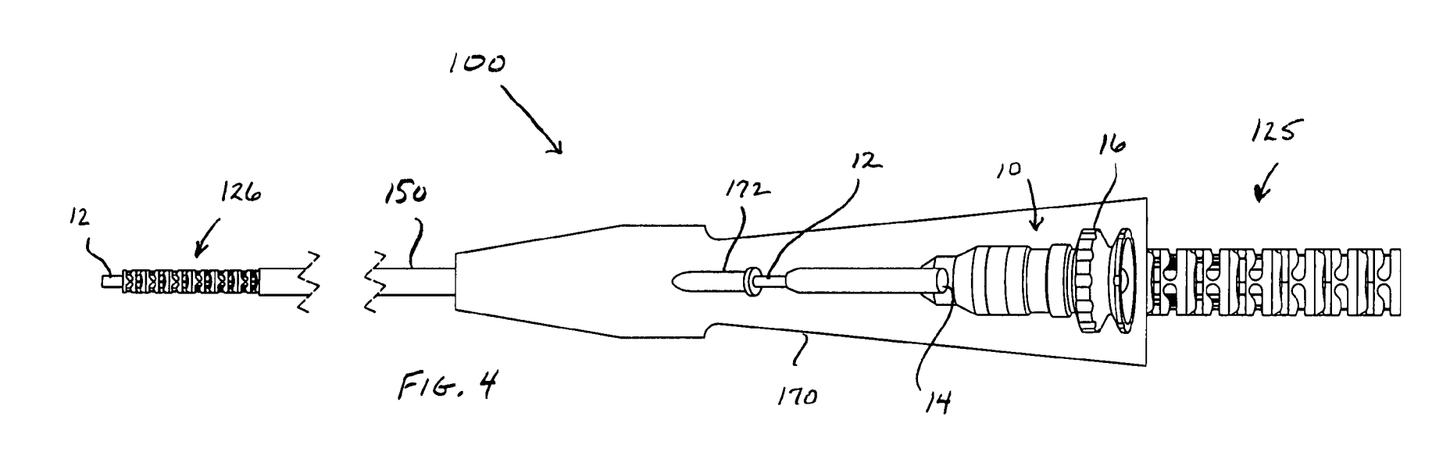
FIG. 4 shows a top view of the sheath and endoscope of FIG. 1, with parts broken away and with the sheath in an unarticulated position.
Figure 5:
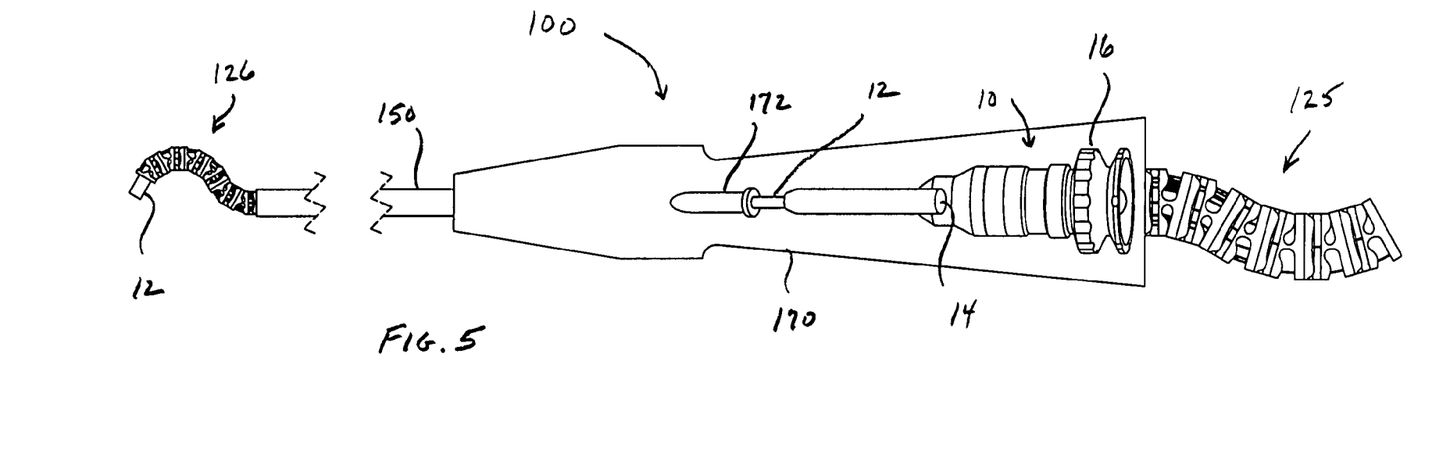
FIG. 5 shows a top view of the sheath and endoscope of FIG. 1, with parts broken away and with the sheath in an articulated position.
Figure 6:
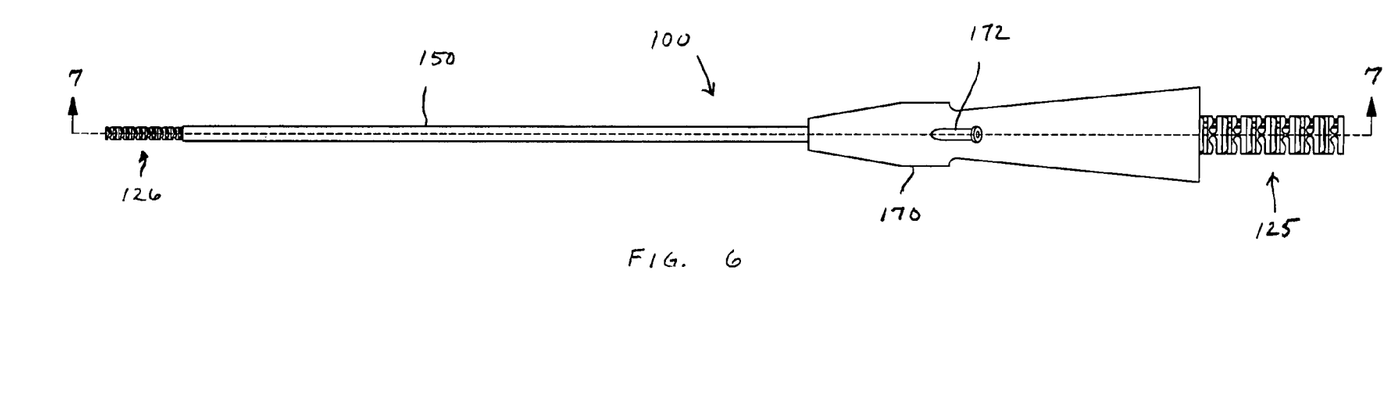
FIG. 6 is a top view of the sheath of FIG. 2.
Figure 7:
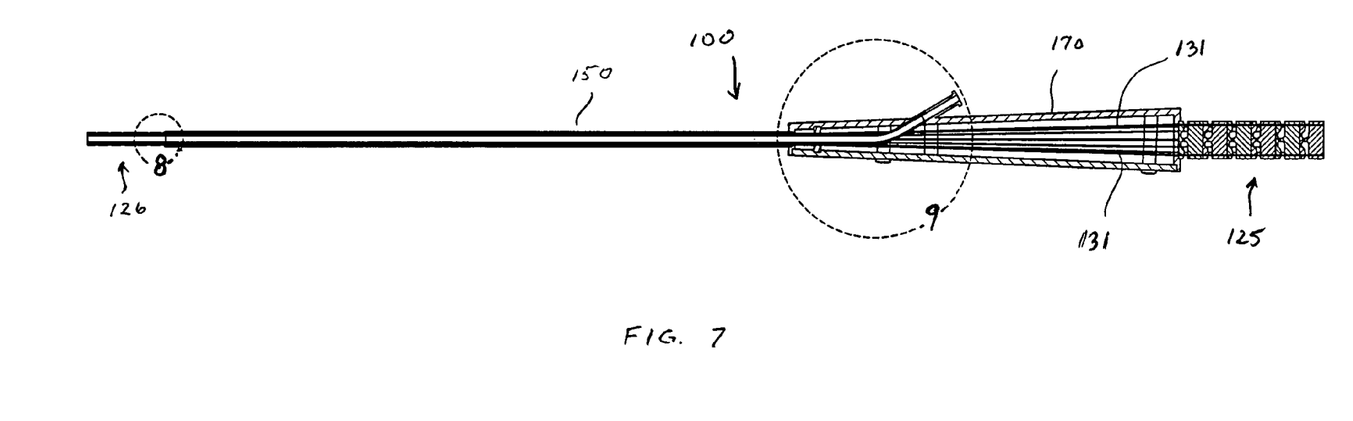
FIG. 7 is a cross-sectional view of the sheath of FIG. 6 taken along the plane designated by line 7-7.
Figure 8:
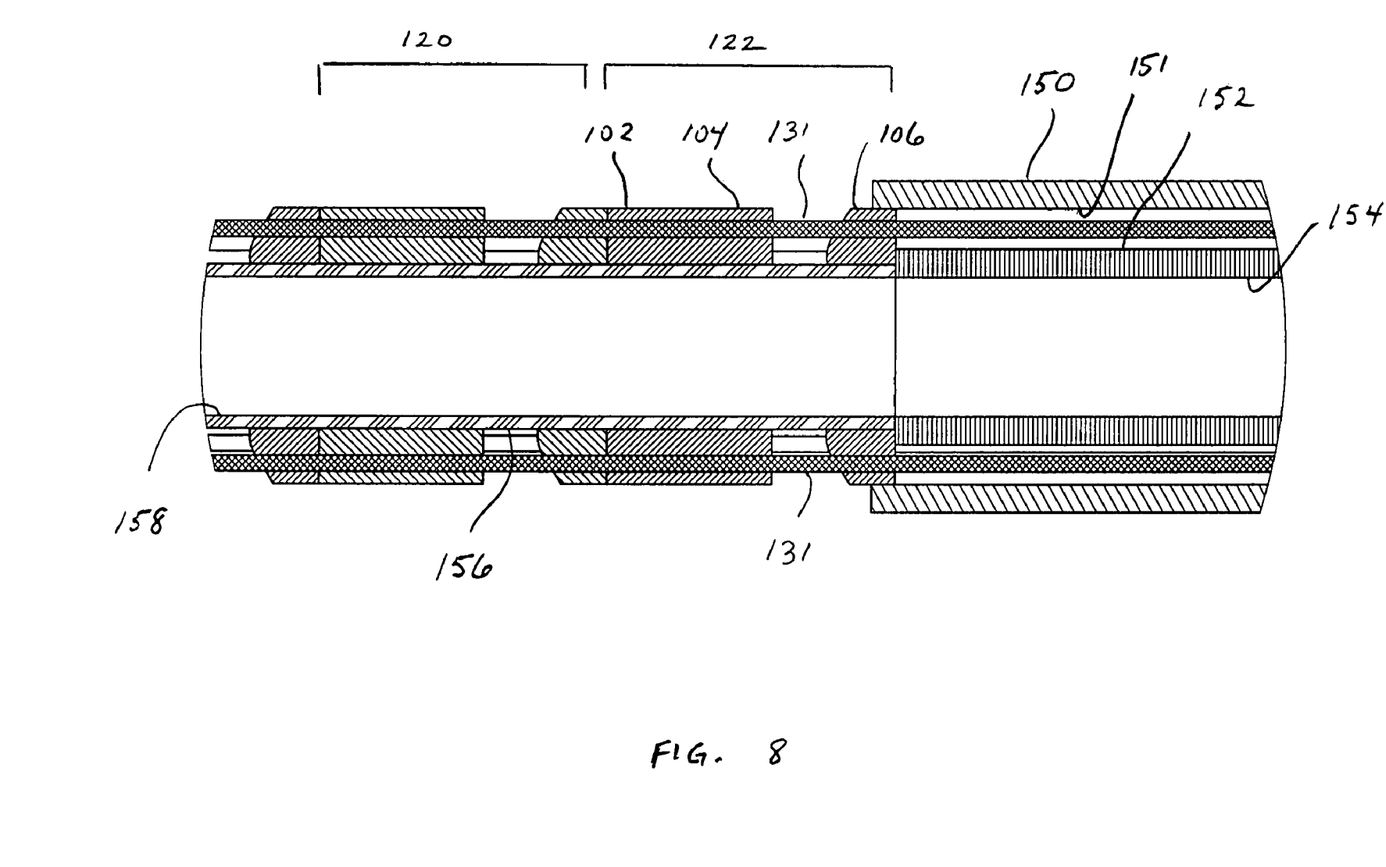
FIG. 8 is an enlarged cross-sectional view of the portion of the sheath of FIG. 7 designated 8, showing part of the distal section of the sheath in greater detail.

FIGS. 4 and 5 further show sheath 100 in greater detail with the proximal and distal ends in a straight, unarticulated configuration (FIG. 4) or in a curved, articulated configuration (FIG. 5). As can be seen, distal section exhibits corresponding, inverse movement relative to the proximal end. Furthermore, the degree of bending or flex of the distal section is proportionally greater than that of the proximal section. This proportional scaling of movement is accomplished by increasing or decreasing the cable channel pattern radius in the links or flexible segments, at either the proximal or distal end, as is further described in pending and commonly owned U.S. application Ser. No. 10/948,911 incorporated herein by reference in its entirety. As can be seen in FIGS. 4 and 5, the radial distance of the cables from central axis of the segments of the proximal section is greater than that in the distal section. The result is that small, controlled movements outside of the body allow for a greater degree of movement at the distal section, which may be advantageous when guiding and navigating a retained endoscope inside the body.

In the proximal and distal sections of sheath 100, there is a one to one, or symmetrical, correspondence of flexible segments. This is not always necessary and there may be applications where it is desirable for a sheath to have asymmetrical arrangements of links or flexible segments at the proximal and distal sections. For example, additional spacer links or flexible segments can be added to the proximal or the distal section, which can be desirable for providing additional length to the proximal or distal sections. In addition the inclusion of additional (or a greater relative number of) of spacer links or flexible segments at either the proximal or distal section allows for the proportional scaling of movement or motion of the corresponding other section. For example, the inclusion of additional spacer links or flexible segments (or a greater relative number of spacer links or flexible segments) at the proximal section would require a more exaggerated movement by the user at the proximal section to achieve the desired motion at the distal section. This could be advantageous in situations where fine, delicate controlled movements were desired, such as, for example, situations where there is a risk that a user may not possess the necessary dexterity to perform the desired procedure absent such proportional scaling of the distal section movement or motion. Alternatively, additional spacer links or flexible segments (or a greater relative number of spacer links or flexible segments) could be provided on the distal section, in which case the degree of distal section movements would be proportionally greater than those of the proximal end, which may also be desirable for particular applications. Spacer links or flexible segments are typically unconstrained, that is, when the distal section of the sheath, contains the individual spacer links or spacer flexible segments the distal section can not resist movement due to laterally applied forces (as opposed to active links or flexible segments which can be constrained to resist movement due to a laterally applied force). Thus, the provision of spacer links or flexible segments decreases the rigidity of the proximal or distal section in those areas that contain such spacer links or flexible segments, which can be desirable when navigation of the sheath through or around sensitive or fragile anatomical structures.

As seen in FIGS. 4 and 5, the resulting directional movement of the distal section 126 is inverted relative to proximal section 125. In other variations, mirrored movement can be achieved by twisting or rotating the cable sets 180 degrees as they pass through the sheath. Other variations on movement can be achieved by twisting or rotating the cables any amount between 0 to 360 degrees.

Figure 9:
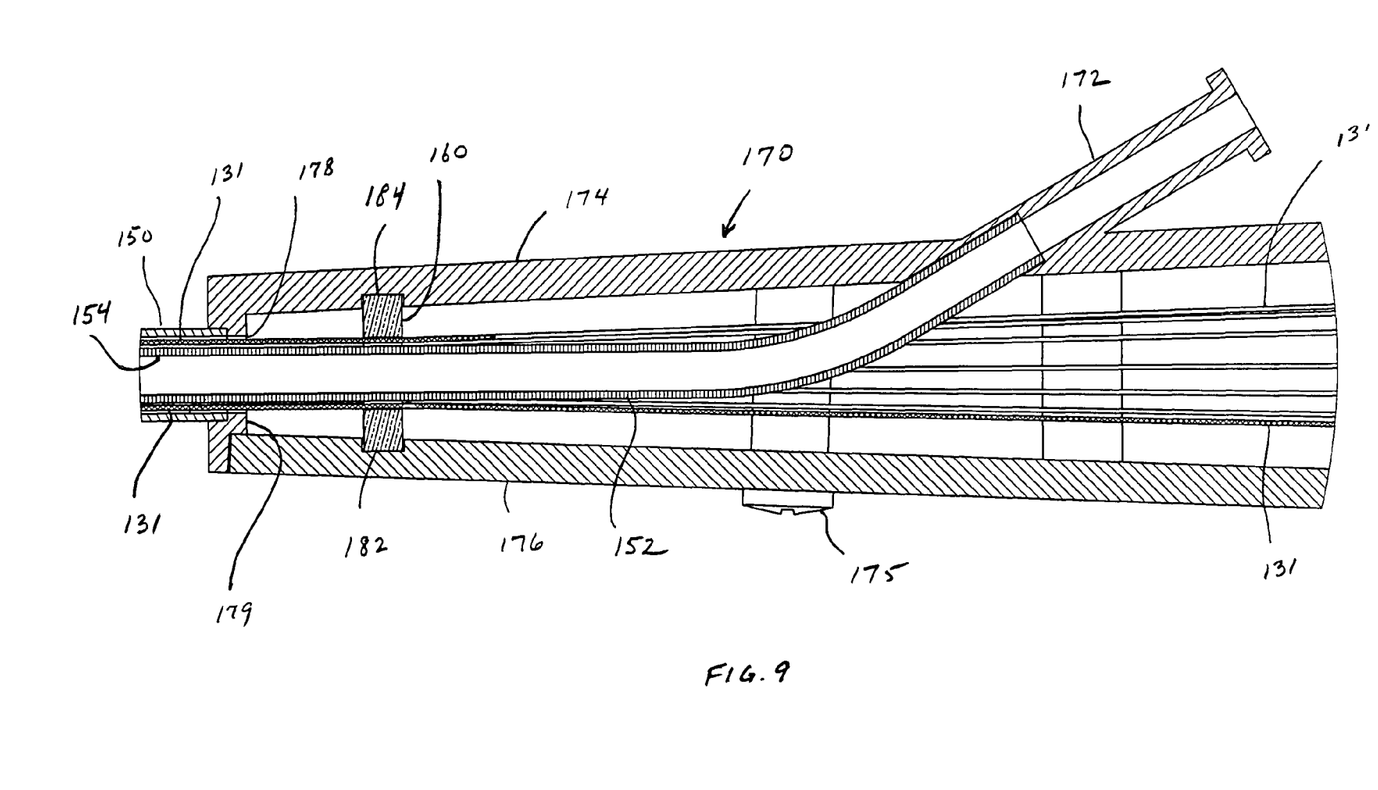
FIG. 9 is an enlarged cross-sectional view of the portion of the sheath of FIG. 7 designated 9, showing part of the handle portion of the sheath in greater detail.

Turning now to FIGS. 6-9, it can be seen that shaft 150 includes a passageway for routing a received endoscope. As FIG. 9 shows in particular detail, handle 170 includes port 172 in communication with inner lumen 154 of shaft tube 152. Shaft tube 152 extends from the inlet port into handle 170 and through shaft 150 until it terminates at the distal end of the shaft where it abuts and is secured to link 106 of flexible segment 122, as shown more clearly in FIG. 8. Alternatively, link 106 could include a counterbore to accept shaft tube 152. Connecting cables, including cables 131, that connect flexible segments of proximal and distal sections 125 and 126 enter the handle from proximal section 125, where they are routed around shaft tube 152, through guide bracket 160, and then through shaft 150 in lumen 151 created by the space between the inner wall of shaft 150 and outer wall of shaft tube 152. Guide bracket 160 is positioned in handle 170 to both center and orient shaft tube 152 as it enters the shaft as well as to orient the cables as they are routed around the shaft tube and into lumen 151 of the shaft. At the distal section, link 106 is attached and secured against both shaft 150 and shaft tube 152. Flexible tube 156 extends through the central channel of the flexible segments of distal section 126 and abuts against shaft tube 154, such that lumen 158 of the flexible tube and lumen 154 of the shaft tube form a continuous lumen for passing the insertion tube of flexible endoscope that extends from inlet port 172 through handle 170 shaft 150, and distal section 126, and that opens at the distal end of distal section. Flexible tube 156 is secured to shaft tube 152 and/or link 106 and is otherwise dimensioned to slip fit within central channel 128 (see FIG. 3C) of the flexible segments of the distal section, such that when the distal section is bent, the links of the flexible segments that form the distal section can move relative to the flexible tube.

Shaft tube 152 can have variable flexibility or stiffness as it extends from the inlet port 172 and handle 170 through the shaft 150. In certain variations, the portion of the shaft tube that extends from inlet port 172 through the handle will be relatively rigid to aid in guiding the endoscope insertion tube through an initial curved pathway as it travels from the port into the shaft. As the shaft tube extends through the shaft, its relative flexibility or stiffness may vary with that of the shaft. In some instances, it may be desirable for the shaft to be relatively stiff which would in essence supply rigidity to an otherwise flexible endoscope deployed through the sheath. This might be advantage for example in laproscopic procedures, where the use of the sheath with a rigid shaft would essentially transform a flexible endoscope into a rigid endoscope. In variations where the shaft is flexible, it may be further advantageous to provide individual lumens to transmit the cables through shaft as an alternative to passing the cables through common lumen 151. Such a configuration can aid in resisting localized shifting and splaying of the cables that may result from flexing of the shaft. Flexible tube 156 on the other hand needs to retain adequate flexibility regardless of the flexibility of the shaft so as not to restrict movement and articulation of distal section 126. Flexible tube 156 is not necessary in variations where the distal section uses a link system with a fully enclosed central channel. It will be appreciated that the shaft length itself can vary, depending on the application. In certain variations, the shaft itself can be formed of links or flexible segments.

Figure 10:
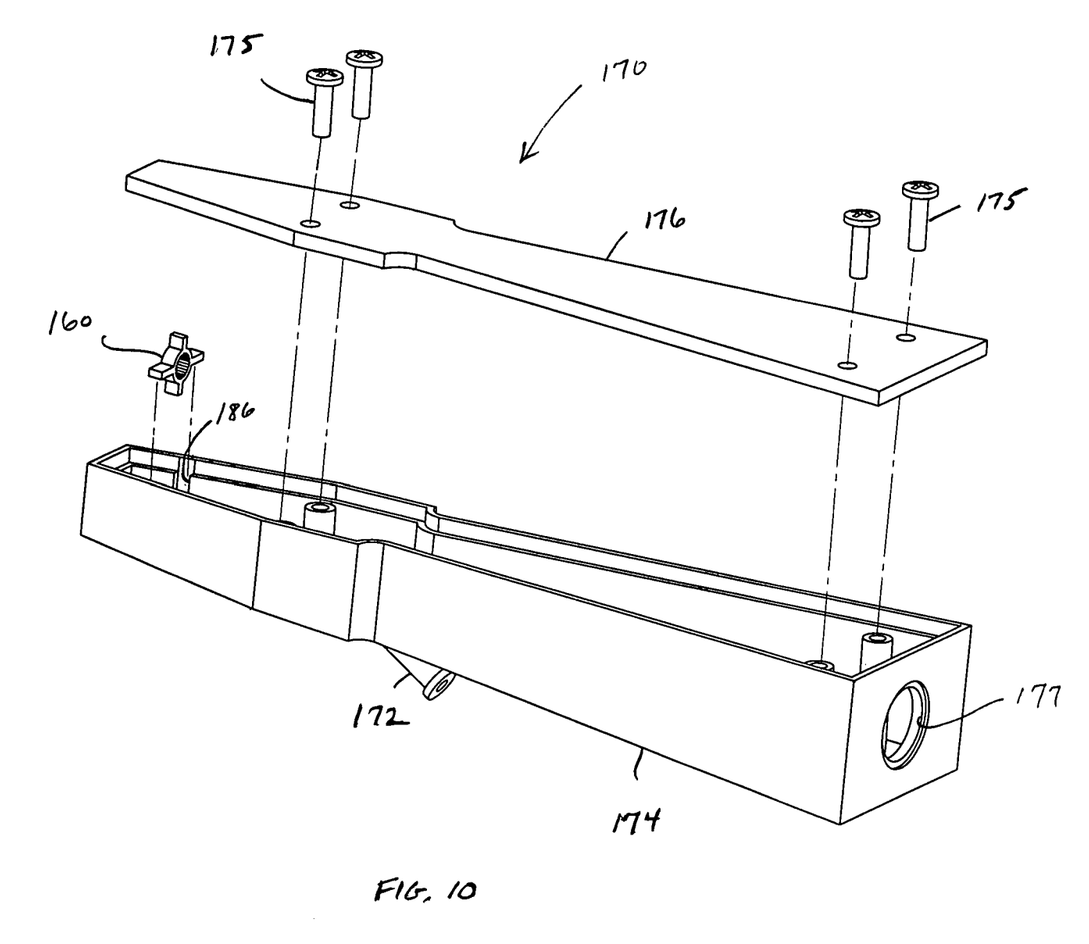
FIG. 10 is an exploded perspective view of the handle portion of the sheath of FIG. 2.
Figure 11A:
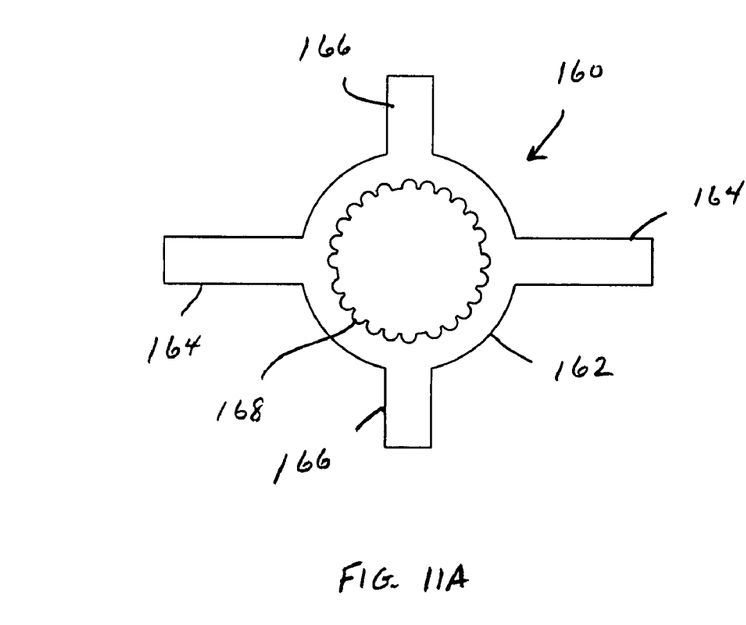
FIGS. 11A and 11B show side and perspective views, respectively, of the cable guide disposed in the handle portion of FIG. 10.
Figure 11B:
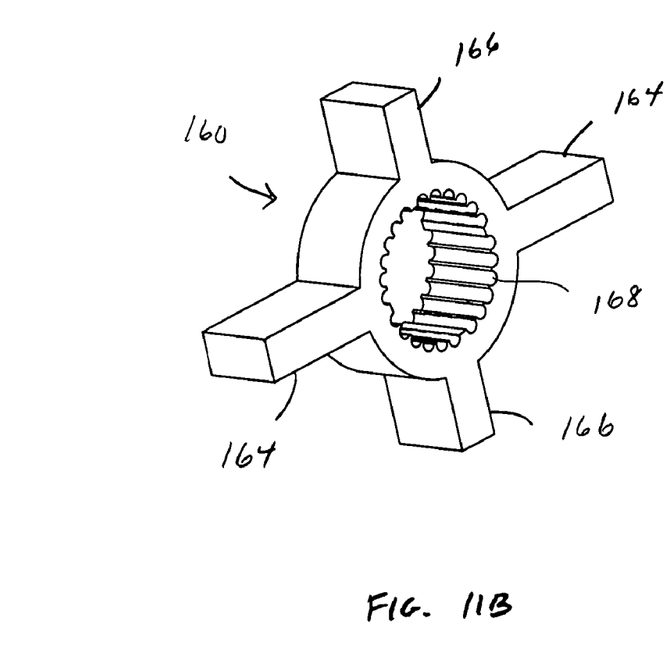

FIG. 10 shows the handle assembly in greater detail. Handle 170 is formed of handle body 174 and handle plate 176 secured together by screws 175. Handle body 174 includes opening 177 at its proximal end. Flexible segment 121 of proximal section 125 attaches at opening 177. Opening 178 at distal end of handle body 174 is similarly configured for receipt and attachment of shaft 150 (see FIG. 9). Handle body 170 further includes guide slots 186 and 184 (see FIG. 9), and handle plate 176 includes guide slot 182, that receive and secure arms of guide bracket 160. Guide bracket 160 is shown in greater detail in FIGS. 11A and 11B. Guide bracket 160 includes center ring 162 with horizontal and vertical arms 164 and 166, respectively, extending from the center ring. Arm 164 and 166 are secured into guide slots 184, 182 and 186. Shaft tube 152 is received through center ring 162 of guide bracket 160 to support the tube and orient it for passage into shaft 150. With shaft tube 152 in place through the central ring of the bracket, grooves 168 together with the outer wall of tube 152 form individual guide channels to guide and orient the connecting cables as they are routed into lumen 151. Alternatively, such guide channels could be integrally formed in face 179 of the distal end of the handle 170. In such a case, a centering channel could also be provided in the face to orient the shaft tube 152.

It will be appreciated that while the provision of handle 172 and inlet port 172 adds a level of convenience, it is not essential. Alternative variations of sheaths according to the invention can have the distal section connect directly to the shaft with the inlet port extending from the shaft itself. In other variations, the inlet port need not extend from the shaft but can simply be an opening to the lumen of the shaft tube that is flush with the shaft surface.

Consistent with the above considerations, the sheath may further be of any size and shape, as the purpose dictates. Links are generally, but need not be, cylindrical, and as previously mentioned include channels for passage of the cables that connect the flexible segment pairs as well as passage of the received endoscope. Depending on the applications, the links and shaft can be dimensioned to accommodate multiple tubes for receiving multiple instruments through the same sheath. The cable channel diameters are usually slightly larger than the cable diameters, creating a slip fit. For typical endoscopes, representative diameters of links may range from about 1 mm to about 3 mm for small endoscopes, about 4 mm to about 8 mm for mid-sized endoscopes, and about 9 mm to about 15 mm or more for large endoscopes. Overall length of the links will vary, usually depending on the bend radius desired between links. Cable diameters may also vary according to the application. For typical endoscopic applications, a representative diameter may range from about 0.1 mm to about 3 mm.

The sheath may be formed of a number of materials known in the art and that can vary according to the application. For ease of manufacture, injection moldable polymers can be used including, e.g., polyethylene or copolymers thereof, polyethylene terephthalate or copolymers thereof, nylon, silicone, polyurethanes, fluoropolymers, poly (vinylchloride); and combinations thereof, or other suitable materials known in the art. Also, for rigid tubes or shafts, stainless steel can be used.

For certain applications a lubricious coating may be placed on the sheath if desired to facilitate advancement of the sheath. The lubricious coating may include hydrophilic polymers such as polyvinylpyrrolidone, fluoropolymers such as tetrafluoroethylene, or silicones. A radioopaque marker may also be included on the distal section of the sheath to indicate the location of the sheath upon radiographic imaging. Usually, the marker will be detected by fluoroscopy.

Cable flexibility may be varied, for instance, by the type and weave of cable materials or by physical or chemical treatments. Usually, cable stiffness or flexibility will be modified according to that required by the intended application of the sheath. The cables may be individual or multi-stranded wires made from material, including but not limited to biocompatible materials such as nickel-titanium alloy, stainless steel or any of its alloys, superelastic alloys, carbon fibers, polymers, e.g., poly (vinylchloride), polyoxyethylene, polyethylene terephthalate and other polyesters, polyolefin, polypropylene, and copolymers thereof; nylon; silk; and combinations thereof, or other suitable materials known in the art.

The cables may be affixed to the links or flexible segments of an active pair according to ways known in the art, such as by using an adhesive or by brazing, soldering, welding, and the like, including methods described in pending and commonly owned U.S. application Ser. Nos. 10/444,769, 10/928,479, and 10/948,911 incorporated herein by reference in their entirety.

Although the many sheaths that have been illustrated in the accompanying figures have a certain number of flexible segments and flexible segment pairs, this is solely for the illustrative purposes. Any number of links and link pairs or flexible segments and flexible segment pairs may be employed, depending on such factors as the intended use and desired length of the sheath.

All publications, patents, and patent applications cited herein are hereby incorporated by reference in their entirety for all purposes to the same extent as if each individual publication, patent or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

The invention claimed is:

1. A sheath for delivery and navigation of a flexible instrument, the sheath comprising:
    an elongate shaft;
    proximal and distal sections having multiple pairs of interconnected links, each link of each pair being maintained in a spaced apart relationship relative to the other link of the pair;
    multiple sets of cables, with each set connecting a discrete pair of links, such that movements of one link of each of the interconnected pairs of links causes corresponding relative movement of the other link of the pair;
    a lumen extending at least partially through the shaft and opening through the distal end of the distal section; and
    an inlet port located between the proximal and distal sections, the inlet port in communication with the lumen, the lumen and inlet port configured for receipt and passage of a flexible instrument.

2. The sheath of claim 1 wherein two or more adjacent links are joined by flexible hinges.

3. The sheath of claim 2 wherein at least one flexible hinge is oriented perpendicular to the longitudinal axis of the shaft.

4. The sheath of claim 2 wherein at least one of the flexible hinges is oriented at an acute angle relative to at least one other flexible hinge.

5. The sheath of claim 2 wherein at least one of the flexible hinges is oriented orthogonal to at least one other flexible hinge.

6. The sheath of claim 2 wherein the flexible hinges are oriented parallel to each other.

7. The sheath of claim 1 wherein movement of the proximal section results in corresponding relative movement of the distal section.

8. The sheath of claim 7 wherein said corresponding relative movement of the distal section is reciprocal to the movement of the proximal section.

9. The sheath of claim 7 wherein said corresponding relative movement of the distal section mirrors the movement of the proximal section.

10. The sheath of claim 1 wherein pairs of links include channels for receipt and passage of sets of cables associated with adjacent pairs of links.

11. The sheath of claim 1 further comprising one or more additional links not connected by discrete sets of cables.

12. The sheath of claim 1 wherein the cables connecting a pair of links are at a different radial distance from the center of the first link of the pair as compared to the second link of the pair.

13. The sheath of claim 1 further comprising a locking mechanism for locking the proximal and distal sections into a fixed position.

14. A method of introducing a flexible endoscope to a desired location within a patient's body comprising the steps of:
    advancing the sheath of claim 1 to a desired location within a patient's body; and
    advancing a flexible endoscope through the sheath.

15. A method of claim 14 further comprising the step of manipulating the proximal section of the sheath to facilitate movement of the endoscope.

16. A system for performing endoscopy comprising:
    the sheath of claim 1; and
    an endoscope received through the lumen of the sheath and with its distal end extending from the distal section of the sheath.

* * * * *